United States Patent [19]

Buck et al.

[11] 4,394,159
[45] Jul. 19, 1983

[54] 2-CHLORO-3-(PHENOXY OR PHENYLTHIO)-6-6-NITRO -ANILINES

[75] Inventors: Wolfgang Buck; Richard Sehring; Gerbert Linden, all of Ingelheim; Sigmund Lust, Darmstadt, all of Fed. Rep. of Germany

[73] Assignee: Celamerck GmbH & Co. KG, Ingelheim, Fed. Rep. of Germany

[21] Appl. No.: 243,385

[22] Filed: Mar. 13, 1981

Related U.S. Application Data

[63] Continuation of Ser. No. 185,799, Sep. 10, 1980, abandoned, which is a continuation of Ser. No. 127,367, Mar. 4, 1980, abandoned, which is a continuation of Ser. No. 57,500, Jul. 13, 1979, abandoned.

[30] Foreign Application Priority Data

Jul. 15, 1978 [DE] Fed. Rep. of Germany ....... 2831262

[51] Int. Cl.³ ..................... E05B 65/08; E05B 63/14; C07C 149/42; C07C 87/60
[52] U.S. Cl. .......................................... 71/98; 71/121; 564/440; 564/441; 71/88; 71/92; 71/94; 71/95; 544/159; 544/358; 546/246; 548/566
[58] Field of Search ............... 564/440, 441, 442, 443; 71/121, 98

[56] References Cited

U.S. PATENT DOCUMENTS 3,914,310 10/1975 Frick et al. ........................... 260/571
3,928,416 12/1975 Bayer et al. ........................... 71/121
4,039,588 8/1977 Wilson et al. ........................... 71/121

FOREIGN PATENT DOCUMENTS 44-13697 6/1960 Japan .................................... 260/571

Primary Examiner—John Doll
Attorney, Agent, or Firm—Hammond & Littell, Weissenberger & Muserlian

[57] ABSTRACT

This invention is directed to 2-chloro-6-nitro-aniline compounds of the formula

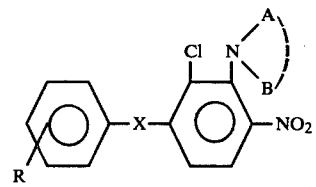

wherein
A represents hydrogen, a straight or branched alkyl radical having from 1 to 6 carbon atoms a cycloalkyl radical having from 3 to 6 carbon atoms, a chlorine-substituted or hydroxyl-sustituted alkyl radical having from 2 to 6 carbon atoms, or an allyl or trifluoroacetyl group,
B represents hydrogen or a methyl, ethyl, n-propyl, or isopropyl group, or
A and B represent together an alkylene radical optionally interrupted by oxygen, =NH or, =NCH₃, and having up to 5 members, or the group
=CH—N(CH₃)₂,
R represents hydrogen, fluorine, chlorine, or bromine or a trifluoromethyl, methyl, or methoxy group, and X represents oxygen or sulphur, and novel herbicidal compositions containing these compounds as active ingredients.

6 Claims, No Drawings

2-CHLORO-3-(PHENOXY OR PHENYLTHIO)-6-6-NITRO-ANILINES

This is a continuation of copending application Ser. No. 185,799, filed Sept. 10, 1980, now abandoned; which in turn is a continuation of application Ser. No. 127,367, filed Mar. 4, 1980, now abandoned; which in turn is a continuation of application Ser. No. 57,500, filed July 13, 1979, now abandoned.

This invention relates to novel substituted 2-chloro-6-nitroanilines, novel herbicidal compositions containing these compounds as active ingredients, and the use of the substituted 2-chloro-6-nitroanilines for the control of plant growth.

More particularly, the substituted 2-chloro-6-nitroanilines according to the invention correspond to the compounds of formula

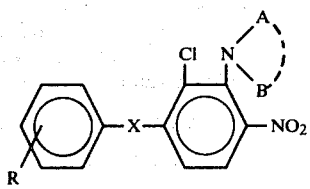
(I)

wherein
A represents hydrogen, a straight or branched alkyl radical having from 1 to 6 carbon atoms, a cycloalkyl radical having from 3 to 6 carbon atoms, an alkyl radical substituted with chlorine or a hydroxyl group and having from 2 to 6 carbon atoms, or an allyl or trifluoroacetyl group, B represents hydrogen or a methyl, ethyl, n-propyl or isopropyl group, or A and B together represent an alkylene radical optionally interrupted by oxygen, =NH, or =NCH₃, and having up to 5 members, or the group =CH—N(CH₃)₂, R represents hydrogen, fluorine, chlorine, or bromine or a trifluoromethyl, methyl, or methoxy group and, X represents oxygen or sulfur.

If A and B together represent an alkyl radical optionally interrupted by a heteroatom, said alkyl radical forms with the nitrogen atom of the group

a heterocyclic group such as, for example

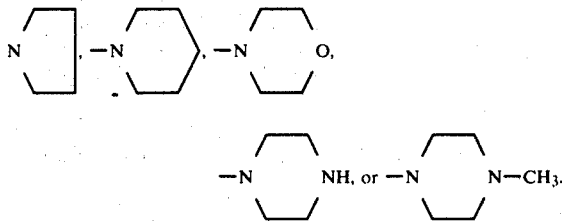

In a preferred embodiment of the compounds of Formula I,

A represents hydrogen, an alkyl radical having from 1 to 4 carbon atoms, or an alkyl radical having from 2 to 4 carbon atoms and substituted with hydroxyl or the group COCF₃, B represents hydrogen, or A and B each represent a methyl group or A and B together represent the group —N=CH—N(CH₃)₂, R represents hydrogen, fluorine, or chlorine, or a methoxy or trifluoromethyl group, and X represents oxygen.

In an especially preferred embodiment of the invention,

A represents hydrogen or a methyl, ethyl, n-propyl, isopropyl, n-butyl, sec.-butyl, tert.-butyl, isobutyl, trifluoroacetyl, B represents hydrogen, R represents hydrogen, fluorine or chlorine, and X represents oxygen.

In another preferred embodiment, when
X represents sulfur, A represents hydrogen, or a methyl, ethyl or allyl group, B represents hydrogen, and R represents hydrogen or fluorine.

The radical R may be situated in the 2-, 3- or 4- position.

It is known that some nitro-substituted diphenyl ethers have herbicidal properties (see K. H. Buchel, Plant Protection and Pest Control, Georg Thieme Verlag, Stuttgart 1977, page 166). It has now been found that the amino-substituted compounds of Formula I are distinguished by outstanding herbicidal activity against a large number of weeds. Moreover, the novel compounds may also be applied selectively in numerous food plant cultivations.

The compounds of this invention are prepared in accordance with known procedures. For example, the compounds of Formula I may be prepared by reacting phenols or thiophenols of the formula

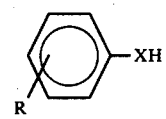
(II)

in which R and X have the above-mentioned meanings, in the presence of an acid-binding agent, or preferably, in the form of a corresponding phenolate or thiophenolate, especially the sodium or potassium salt, with a 2,3-dichloro-6-nitroaniline of the formula

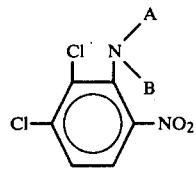
(III)

wherein A and B have the above-mentioned meanings, at a temperature between room temperature, i.e., about 20° C., and about 120° C., preferably between about 50° and 100° C.

A solvent inert under the reaction conditions serves as the reaction medium. Suitable such solvents include acetonitrile and dimethyl formamide, as well as, e.g., methylethyl ketone, dimethyl sulphoxide, and N-methyl pyrrolidone.

The starting materials of Formulas II and III can be obtained by conventional processes. For the preparation of the anilines of Formula III, some of which are novel, 2,3,4-trichloronitrobenzene may be reacted with 2 moles of the amine HNAB, wherein A and B are as defined above, in a suitable solvent. One mole of the amine HNAB may advantageously be replaced by a tertiary amine.

In general, the anilines of Formula III may be used without purification for further reaction. Occasionally, however, it is advantageous to purify the aniline of Formula III by distillation, recrystallisation, or column chromatography. The use of a purified aniline of Formula III leads, in general, to a better total yield and aids in providing directly a sufficiently pure final product.

For the preparation of those compounds of Formula I in which A represents a chlorine-substituted alkyl radical, the hydroxyl group in the corresponding N-hydroxyalkyl compounds of Formula I is replaced by chlorine with conventional agents. This reaction can be effected by processes known per se, optionally in an inert solvent, such as, for example, toluene. If phosphorus pentachloride is employed, the reaction proceeds with spontaneous heating; however, if thionyl chloride is used, heating is advantageous.

The starting materials to prepare the compounds of Formula I wherein A represents a chlorine-substituted alkyl group radical, may be obtained by conventional processe such as that mentioned above.

The compounds of Formula I in which A represents trifluoroacetyl group or A and B together represent the group $=CH-N(CH_3)_2$, may be obtained from corresponding compounds in which A or A and B represent hydrogen by reaction with trifluoroacetanhydride or with dimethyl formamide/phosphoroxy chloride or a dimethyl formamide dialkyl acetal.

To introduce the trifluoroacetyl group, a starting compound, i.e., a compound of Formula I wherein A is hydrogen, is appropriately reacted with the trifluoroacetanhydride in an inert solvent, for example, toluene, at room temperature or with heating.

For preparation of the amidine, a reaction mixture comprising a compound of Formula I wherein A or B are both hydrogen is heated strongly, for example, to about 80° to 150° C. Suitable solvents include dimethyl formamide and dimethyl sulfoxide.

The starting substances, compounds of Formula I wherein A or both A and B represent hydrogen, may be obtained according to the procedure described above for the preparation of the compounds of Formula I.

As described more fully below, the compounds of Formula I are useful per se. These compounds are additionally useful in that they represent valuable intermediates for the preparation of plant protective agents and medicinal substances, because the amino and nitro groups can be readily modified according to known procedures.

The following examples further illustrate the present invention and will enable others skilled in the art to understand it more completely. It should be understood, however, that the invention is not limited solely to the particular examples given below.

EXAMPLE I 2,3-Dichloro-6-nitro-N-isobutylaniline (a compound of Formula III

Forty-eight grams of isobutylamine and 75.5 gm of 2,3,4-trichloronitrobenzene were dissolved in 200 ml of toluene and kept at room temperature for 3 days. The mixture was then treated with a further 5 gm of isobutylamine and heated to 60° C. for 4 hours. The toluene solution was shaken with water, dried, and evaporated. The yield was 86 gm of 2,3-dichloro-6-nitro-N-isobutylaniline (98% of theory), which was obtained as a brownish oil.

By use of analogous procedures, the compounds shown in the following table were also prepared:

TABLE 1

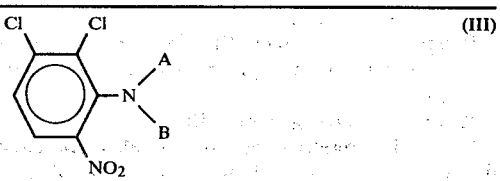

(III)

| Example | A | B | M.p. or $n_D^{20}$ | Solvent | Reaction Temp. | Reaction Time |
|---|---|---|---|---|---|---|
| 2 | H | H | 166° C. | DMSO | 50° C. | 24 hrs. |
| 3 | CH$_3$ | H | 60° C. | DMSO | 10° C. | 3 hrs. |
| 4 | C$_2$H$_5$ | H | 51° C. | DMSO | RT | 4 hrs. |
| 5 | C$_2$H$_5$ | C$_2$H$_5$ | 1.564 | DMSO | RT | 5 hrs. |
| 6 | CH$_3$ | CH$_3$ | 1.590 | DMF | RT | 5 hrs. |
| 7 | C$_3$H$_7$ | H | 1.627 | DMSO | RT | 3 hrs. |
| 8 | i-C$_3$H$_7$ | H | 1.615 | DMSO | RT | 26 hrs. |
| 9 | n-C$_4$H$_9$ | H | 1.613 | DMSO | RT | 2 days |
| 10 | n-C$_3$H$_7$ | n-C$_3$H$_7$ | 1.557 | WITHOUT | 80° C. | 9 hrs. |
| 11 | (CH$_3$)$_2$CHCH$_2$ | H | 1.605 | toluene | RT | 3 days |
| 12 | H$_5$C$_2$ CH—CH$_3$ | H | 1.603 | toluene | 80° C. | 8 hrs. |
| 13 | HOCH$_2$CH$_2$ | H | 94–5° C. | DMSO | RT | 16 hrs. |
| 14 | (CH$_2$)$_5$ | | 73–4° C. | dioxane | RT | 3 days |
| 15 | (CH$_2$)$_4$ | | 1.600 | toluene | RT | 2 days |
| 16 | —(CH$_2$)$_2$—N(CH$_3$)—(CH$_2$)$_2$— | | 93–4° C. | dioxane | 100° C. | 10 hrs. |
| 17 | —(CH$_2$)$_2$—O—(CH$_2$)$_2$— | | 107–8° C. | dioxane | 100° C. | 10 hrs. |
| 18 | n-C$_6$H$_{13}$ | H | 1.591 | toluene | RT | 2 days |
| 19 | n-C$_5$H$_{11}$ | H | 1.593 | toluene | RT | 2 days |

TABLE 1-continued

| Example | A | B | M.p. or $n_D^{20}$ | Solvent | Reaction Temp. | Time |
|---|---|---|---|---|---|---|
| 20 | ⬡—H | H | 1.615 | toluene | RT | 3 days |
| 21 | CH₂=CH—CH₂— | H | 1.636 | toluene | RT | 3 days |

DMSO: Dimethyl sulphoxide
DMF: Dimethyl formamide
RT: Room temperature

EXAMPLE 22

(a) 2,3-Dichloro-6-nitroaniline

An amount of 453 gm of 2,3,4-trichloronitrobenzene (2 mole) were dissolved in 2 liters of dimethyl sulfoxide and poured into an autoclave holding 5 liters. Two hundred milliliters of liquid ammonia (8 mole) were added. After the autoclave was closed, the mixture was heated to 50° C. with stirring or shaking and kept at this temperature for 24 hours After cooling and ventilation of the autoclave, the solution obtained was poured with precipitated NH₄Cl onto 8 liters of water. The precipitated product was extracted, washed with water, and dried at 50° C. overnight. Four hundred grams (96.5% of theory) of a yellow crystalline product which melts at 161°-164° C., were obtained. This product was sufficiently pure for further reactions. However, it can also be purified by recrystallization, for example, from methyl isobutyl ketone. The yield from such recrystallization was 77% of theory, m.p. 166°-167° C.

(b) 2-Chloro-3-phenoxy-6-nitroaniline

(i) From crude 2,3-dichloro-6-nitroaniline

A solution of 103.5 gm of 2,3-dichloro-6-nitroaniline (0.5 mole) and 63.8 gm of sodium phenolate (0.55 mol) in 1000 ml of acetonitrile was refluxed for 5 hours and subsequently evaporated. The residue was dissolved in 750 ml of chloroform, and the solution was shaken twice, each time with 200 ml of water.

After the chloroform solution was dried, it was evaporated. The residue, 130 gm of a brown oil, was dissolved hot in about 700 ml of isopropanol, and the solution was cooled with stirring. The product was precipitated and then extracted. Ninety-eight grams of yellow crystals (74% of theory) of 2-chloro-3-phenoxy-6-nitroaniline were obtained. The melting point was 83° C. The NMR spectrum confirmed the structure.

(ii) From purified 2,3-dichloro-6-nitroaniline

An amount of 15.5 gm of purified 2,3-dichloro-6-nitroaniline was dissolved in 75 ml of dimethyl sulphoxide, mixed with 7.8 gm of phenol and 11.5 gm of ground potassium carbonate, and stirred for 8 hours at 50° C. The mixture was subsequently acidified with glacial acetic acid and the product was precipitated with ice water, extracted, and dried. An amount of 19.5 gm of final product was obtained (98% yield relative to the 2,3-dichloro-6-nitroaniline used). The product was in the form of yellow crystals, m.p. 80°-82° C.

EXAMPLE 23

2-Chloro-3-phenoxy-6-nitroaniline

A solution of 911 gm (4 mole) of 2,3,4-trichloronitrobenzene was dissolved in 4 liters of dimethyl sulfoxide and mixed in a 10-liter autoclave with 400 ml of liquid ammonia. The autoclave was closed and kept at 50° C. for 24 hours, a pressure of 5.3 bars being set. After cooling of the mixture and ventilation of the pressure vessel, the mixture was removed and stirred in a 15 liter vessel with 400 gm of 40% (% by weight) sodium hydroxide solution. In so doing, ammonia escaped and was drawn off. Four hundred sixteen grams of phenol (4.4 mol) were then added to the solution which was heated to 50° C., and 440 gm of 40% by weight solution of sodium hydroxide solution were dropped therein. The mixture was stirred for 7 hours at 50°-60° C. To complete the reaction, 41 gm of phenol and 44 gm of 40% by weight solution of sodium hydroxide were added again, and the mixture was kept at 60° C. for a further 3 hours. The mixture was allowed to cool and was acidified with 100 ml of glacial acetic acid, and the product was precipitated with ice water by trituration. The yellowy brown solid crude product was extracted, washed with water, and dried. The crude product (980 gm m.p. 70°-78° C.) was recrystallized from 2.5 liters of isopropanol. The yield was 800 gm (75.5% of theory) of a yellowy brown solid, m.p. 81.5°-83.5° C.

EXAMPLE 23

2-Chloro-3-phenylthio-6-nitro-N-methylaniline

An amount of 2.9 gm of sodium thiophenolate was added to a solution of 4.4 gm (0.02 mol) of 2,3-dichloro-6-nitro-N-methylaniline dissolved in 50 ml of acetonitrile. The mixture was refluxed for half an hour and subsequently evaporated, and the residue was taken up with chloroform and water. The chloroform layer was separated, dried, and evaporated. Six grams of brown oil, which crystallized with isopropanol, were obtained. The yield from the crystallization was 4 gm of product (67.5% of theory) in the form of yellow crystals, m.p. 79° C.

| ELEMENTAL ANALYSIS | C | H | N | Cl | S |
|---|---|---|---|---|---|
| Calculated: | 52.7% | 3.72% | 9.47% | 12.05% | 10.9% |
| Found: | 52.73% | 3.75% | 9.55% | 12.00% | 10.82% |

EXAMPLE 24

2-Chloro-3-(3-chlorophenoxy)-6-nitro-trifluoroacetaniline

Ninety grams of 2-chloro-3-(3-chlorophenoxy)-6-nitroaniline were partially dissolved in 500 ml of toluene.

Seventy grams of trifluoroacetanhydride were added thereto with stirring over 15 minutes. The mixture was stirred overnight. The solvent was then distilled off, the residue was dissolved in 300 ml of ether, and the product was precipitated by the addition of benzine with trituration, extracted, and dried. The yield was 101 gm (85% of theory) of light beige, crystalline solid, m.p. 99°–101° C.

EXAMPLE 25

1,1-Dimethyl-3-(2-chloro-3-phenoxy-6-nitrophenyl)formamidine

An amount of 7.9 gm of 2-chloro-3-phenoxy-6-nitroaniline was heated to 100°–110° C. for 8 hours with 10 ml of dimethyl formamide and 10 ml of dimethyl formamide dimethyl-acetal. The mixture was subsequently evaporated in vacuo at 90° C. A reddish brown, viscous mass was obtained which solified at about 0° C.

Elemental analysis confirmed the specified formula:

|  | C | H | N | Cl |
|---|---|---|---|---|
| Calculated: | 56.34% | 4.41% | 13.14% | 11.09% |
| Found: | 56.34% | 4.39% | 13.17% | 11.09% |

EXAMPLE 26

2-Chloro-3-(4-chlorophenoxy)-6-nitro-N-2-chloroethylaniline

An amount of 4.5 gm of 2-chloro-3-(4-chlorophenoxy)-6-nitro-N-2-hydroxyethylaniline was dissolved in 40 ml of toluene and mixed with 2.9 gm of PCl5, spontaneous heating and gas generation taking place. After 30 minutes the mixture was shaken with water and sodium bicarbonate solution and is evaporated. 3.6 gm of a yellowy brown oil were obtained (76% of theory).

EXAMPLE 27

2-Chloro-3-phenylthio-6-nitroaniline

A mixture of 103.5 gm of 2,3-dichloro-6-nitroaniline (0.5 mol) and 72.5 gm of sodium thiophenolate (0.55 mol) was dissolved in 800 ml of acetonitrile, and the solution was refluxed for 5 hours. The mixture was then processed according to the procedure set forth in Example 22 (b)(i). The yield was 108 gm of ochre-coloured, crystalline product (77% of theory), m.p. 144°–146° C.

EXAMPLE 28

2-Chloro-3-(3-chlorophenoxy)-6-nitroaniline

A mixture of 103.5 gm of 2,3-cichloro-6-nitroaniline (0.5 mol) and 82.8 gm of sodium 3-chlorophenolate in 500 ml of dimethyl formamide was heated for one hour at 100° C. After evaporation of the solution, the residue was taken up in chloroform and washed with water. The dried chloroform solution was evaporated. The oil residue was dissolved hot in about 700 ml of isopropanol. Upon cooling, the product crystallized. The yield was 90 gm of an ochre-colored, crystalline substance with a melting point of 101°–102° C.

EXAMPLE 29

2-Chloro-3-(4-fluorophenoxy)-2-nitro-N-ethylaniline

An amount of 23.5 gm (0.1 mol) of N-ethyl-2-, 3-dichloro-6-nitroaniline was dissolved in 150 ml of dimethyl sulphoxide in a 250 ml three-necked flask. After addition of 12.3 gm (0.11 mol) of 4-fluorophenol and 15.2 gm (0.11 mol) of potassium carbonate, the mixture was stirred for 5 hours at 80° C. The product was precipitated from the cooled solution by the slow addition of ice water and was recrystallized after extraction with isopropanol. The yield was 17 gm (54.7% of theory) of ochre-colored, crystalline product, m.p. 69°–70° C.

| ELEMENTAL ANALYSIS: | C | H | N | Cl | F |
|---|---|---|---|---|---|
| Calculated: | 50.99% | 2.85% | 9.92% | 12.55% | 6.72% |
| Found: | 51.17% | 3.01% | 9.92% | 12.35% | 6.54% |

In accordance with procedures analogous to those described above in Examples 22–29, the compounds set forth in the following table were obtained.

TABLE 2

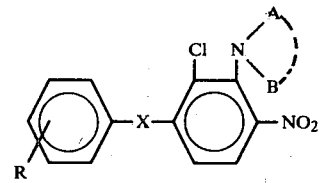

|  |  |  |  |  | M.p. | Rf Values* | |
|---|---|---|---|---|---|---|---|
| EXAMPLE | R | X | A | B | [°C.] | (a) | (b) |
| 30 | 4-Cl | O | H | H | 108 | — | — |
| 31 | 4-CH3 | O | H | H | 97–98 | — | — |
| 32 | 4-OCH3 | O | H | H | 113–115 | — | — |
| 33 | 3-CH3 | O | H | H | 112–114 | — | — |
| 34 | 4-Cl | S | H | H | 136–138 | — | — |
| 35 | 4-F | O | H | H | 111–113 | — | — |
| 36 | 2-Cl | O | H | H | 85–86 | — | — |

TABLE 2-continued

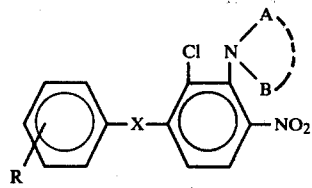

| EXAMPLE | R | X | A | B | M.p. [°C.] | Rf Values (a) | (b) |
|---|---|---|---|---|---|---|---|
| 37 | 4-Br | O | H | H | 118 | — | — |
| 38 | 3-CF$_3$ | O | H | H | 92–93 | — | — |
| 39 | 3-F | O | H | H | 58–60 | — | — |
| 40 | 2-F | O | H | H | 104–105 | — | — |
| 41 | 4-Cl | O | COCF$_3$ | H | 135–137 | — | — |
| 42 | 4-CH$_3$ | O | COCF$_3$ | H | 155 | — | — |
| 43 | H | O | CH$_3$ | H | 76 | — | — |
| 44 | 4-Cl | O | CH$_3$ | H | 75–77 | — | — |
| 45 | 3-Cl | O | CH$_3$ | H | Oil | — | — |
| 46 | 4-CH$_3$O | O | CH$_3$ | H | 100–101 | — | — |
| 47 | 4-F | O | CH$_3$ | H | 103 | — | — |
| 48 | H | O | C$_2$H$_5$ | H | Oil | — | — |
| 49 | 4-F | O | C$_2$H$_5$ | H | 71–72 | — | — |
| 50 | 4-Cl | O | C$_2$H$_5$ | H | 72–74 | — | — |
| 51 | 4-CH$_3$ | O | C$_2$H$_5$ | H | 51–52 | — | — |
| 52 | H | S | C$_2$H$_5$ | H | Oil | 0.6 | 0.45 |
| 53 | 3-CH$_3$ | O | C$_2$H$_5$ | H | Oil | 0.61 | 0.445 |
| 54 | 3-Cl | O | C$_2$H$_5$ | H | Oil | 0.60 | 0.48 |
| 55 | 4-CH$_3$O | O | C$_2$H$_5$ | H | 47–48 | — | — |
| 56 | 4-Br | O | C$_2$H$_5$ | H | 57–59 | — | — |
| 57 | 2-Cl | O | C$_2$H$_5$ | H | Oil | 0.58 | 0.045 |
| 58 | 3-CF$_3$ | O | C$_2$H$_5$ | H | Oil | 0.60 | 0.49 |
| 59 | H | O | n-C$_3$H$_7$ | H | Oil | 0.615 | 0.47 |
| 60 | H | O | —CH(CH$_3$)$_2$ | H | Oil | 0.61 | 0.45 |
| 61 | H | O | CH$_3$ | CH$_3$ | 69–72 | — | — |
| 62 | 4-F | O | CH$_3$ | CH$_3$ | 43–44 | — | — |
| 63 | H | O | C$_2$H$_5$ | C$_2$H$_5$ | Oil | — | — |
| 64 | 4-Cl | O | n-C$_3$H$_7$ | H | Oil | 0.63 | 0.525 |
| 65 | 4-Cl | O | —CH(CH$_3$)$_2$ | H | Oil | 0.63 | 0.50 |
| 66 | H | O | n-C$_4$H$_9$ | H | Oil | 0.625 | 0.50 |
| 67 | 4-F | O | n-C$_3$H$_7$ | H | Oil | 0.61 | 0.48 |
| 68 | 4-F | O | CH(CH$_3$)$_2$ | H | Oil | 0.62 | 0.46 |
| 69 | 4-CH$_3$ | O | n-C$_3$H$_7$ | H | Oil | 0.64 | 0.47 |
| 70 | H | O | n-C$_3$H$_7$ | nC$_3$H$_7$ | Oil | | |
| 71 | 4-F | O | n-C$_4$H$_9$ | H | Oil | 0.63 | 0.505 |
| 72 | 4-Cl | O | n-C$_4$H$_9$ | H | Oil | 0.64 | 0.55 |
| 73 | 4-CH$_3$ | O | n-C$_4$H$_9$ | H | Oil | 0.64 | 0.495 |
| 74 | 4-CH$_3$O | O | n-C$_3$H$_7$ | H | Oil | 0.59 | 0.29 |
| 75 | 4-CH$_3$O | O | —CH(CH$_3$)$_2$ | H | Oil | 0.57 | 0.28 |
| 76 | 4-CH$_3$O | O | n-C$_4$H$_9$ | H | Oil | 0.555 | 0.32 |
| 77 | 4-Br | O | n-C$_3$H$_7$ | H | Oil | 0.59 | 0.52 |
| 78 | 4-Br | O | n-C$_4$H$_9$ | H | Oil | 0.61 | 0.555 |
| 79 | 3-CF$_3$ | O | n-C$_3$H$_7$ | H | Oil | 0.59 | 0.53 |
| 80 | H | O | CH$_2$CH(CH$_3$)$_2$ | H | Oil | 0.60 | 0.51 |
| 81 | H | O | —CHC$_2$H$_5$<br>    |<br>   CH$_3$ | H | Oil | 0.61 | 0.50 |
| 82 | 4-F | O | CH$_2$CH(CH$_3$)$_2$ | H | Oil | 0.60 | 0.525 |
| 83 | 4-F | O | CHC$_2$H$_5$ CH$_3$ | H | Oil | 0.62 | 0.515 |
| 84 | 4-Cl | O | CH$_2$CH(CH$_3$)$_2$ | H | Oil | 0.63 | 0.56 |
| 85 | H | O | C$_2$H$_4$OH | H | Oil | 0.445 | 0.01 |
| 86 | H | S | n-C$_3$H$_7$ | H | Oil | 0.62 | 0.49 |
| 87 | H | S | —CH(CH$_3$)$_2$ | H | 56–57 | | |
| 88 | H | S | n-C$_4$H$_9$ | H | Oil | 0.63 | 0.52 |
| 89 | H | S | CH$_2$CH(CH$_3$)$_2$ | H | Oil | 0.78 | 0.52 |
| 90 | H | O | —C$_2$H$_4$OH | H | Oil | 0.44 | 0.01 |
| 91 | 4-CH$_3$O | O | CH$_2$CH(CH$_3$)$_2$ | H | Oil | 0.58 | 0.35 |
| 92 | H | O | —(CH$_2$)$_4$— | | 106–107 | — | — |
| 93 | H | O | —(CH$_2$)$_5$— | | 98–99 | — | — |
| 94 | H | O | —(CH$_2$)$_2$—N—(CH$_2$)$_2$—CH$_3$ | | 99–101 | — | — |
| 95 | H | O | —(CH$_2$)$_2$—O—(CH$_2$)$_2$— | | 109–110 | — | — |
| 96 | H | S | CH$_3$ | H | 128–130 | — | — |
| 97 | 4-F | O | nC$_6$H$_{13}$ | H | Oil | 0.63 | 0.57 |
| 98 | H | O | nC$_5$H$_{11}$ | H | Oil | 0.62 | 0.54 |
| 99 | 4-Cl | O | —(CH$_2$)$_5$— | | 105 | — | — |
| 100 | 4-F | O | nC$_5$H$_{11}$ | H | Oil | 0.62 | 0.56 |

TABLE 2-continued

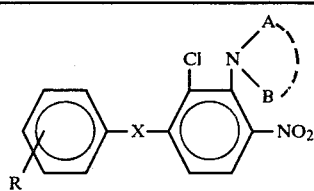

| EXAMPLE | R | X | A | B | M.p. [°C.] | Rf Values* (a) | (b) |
|---|---|---|---|---|---|---|---|
| 101 | H | O | –⟨H⟩ | H | Oil | 0.61 | 0.52 |
| 102 | H | S | —CH₂—CH=CH₂ | H | Oil | 0.72 | 0.48 |

*Rf (a) values relate to the acetone/n-heptane system (1:1 v/v);
Rf (b) values relate to toluene as the eluant.

As indicated above, it has been discovered that the compounds embraced by Formula I have very effective herbicidal properties. The compounds of Formula I have a marked selective herbicidal effect, especially against weeds, such as meadow foxtail, wild oats, rye grass, and wild millet. Selectivity is so pronounced that, even when higher quantities are used, dicotyledon food plants are only slightly affected. Even in some fields of monocotyledon food plants, such as corn, rice, barley or oats, weeds can be combatted with the active substances according to the present invention.

For herbicidal purposes, the compounds of the Formula I are processed in known manner into customary formulations with conventional auxiliary and/or carrier substances, for example, into concentrates such as emulsion concentrates or wettable, or suspension powders, in which the active ingredient content is between about 10 and 95% by weight and which are adjusted to the desired concentration of active ingredient for discharge with water. However, preparations may also be prepared which are applied undiluted as, for example, dusting powders, granulates, or solutions. In these cases, the content of active ingredient is between about 0.2 and 20% by weight, preferably between about 0.5 and 3% by weight, based on the weight of the total preparation.

The concentrates are diluted with water to the desired concentration for application, generally about 0.01 to 3% by weight.

The following examples illustrate herbicidal compositions containing a compound of the Formula I as an active ingredient.

EXAMPLE 103

Wettable powder

25% by weight of 2-chloro-3-phenoxy-6-nitroaniline,
55% by weight of kaolin
10% by weight of colloidal silicic acid,
9% by weight of calcium lignin sulfonate (dispersing agent),
1% by weight of sodium tetrapropylenebenzene sulfonate (wetting agent).

The constituents are admixed are ground, and the powder is suspended in water for application in such a way that a concentration of active substance of about 0.05 to 5% is obtained.

EXAMPLE 104

Emulsion concentrate

20% by weight of 2-chloro-3-phenoxy-6-nitroaniline,
70% by weight of a liquid solvent mixture of high-boiling point aromatic hydrocarbons (Shellsol A),
6.5% by weight of Tensiofix AS (emulsifier)
3.5% by weight of Tensiofix DS (emulsifier).

The concentrate constituents are admixed and combined in known manner, the concentrate is mixed with water for spray application in such a way that a concentration of active substance of about 0.05 to 5% by weight is obtained.

EXAMPLE 105

Dusting powder

1% by weight of 2-chloro-3-phenoxy-6-nitroaniline,
98% by weight of talcum,
1% by weight of methyl cellulose.

The constituents are admixed and ground homogeneously to make the dusting powder.

Other compounds of Formula I can readily be substituted for 2chloro-3-phenoxy-6-nitroaniline in any of the Examples 103 to 105.

It is also possible, and in some cases advantageous, to use the active ingredients according to the invention together with other herbicides, for example, with triazine herbicides such as Simazine or Atrazine in corn, with urea herbicides such as, e.g., Linurone or Monolinurone in potatoes or corn, with dinitroaniline herbicides such as Dinitramine or Trifluoraline in corn, with diphenyl ethers,—e.g., Nitrophene in rice, and with carboxylic acid amides such as Alachlor in onions.

The compounds according to the invention may be applied by the pre-germination method or by the post-germination method. For example, mustard, amaranth, camomile, barnyard grass and field foxtail may be controlled outdoors by the pre-germination method with an applied quantity of 1 kg/ha of 2-chloro-3-phenoxy-6-nitroaniline. In so doing, the compatibility in potatoes and maize is over 3 kg/ha and in what and peas over 2.5 kg/ha. Application of the above-mentioned compounds after germination enables, e.g., galium and field foxtail to be controlled with 1 kg/ha and also mustard, amaranth, and camomile to be controlled with a slightly higher dose. Apart from in the abovementioned cultivations, the compounds according to the invention may also be employed, for example, in barley, beet, and rice.

The following table lists results of green-house tests for a representative selection of compounds according to the invention on important weeds. The applied quantities are given in kg/ha.

A: *Sinapis alba* (white mustard)
b: *Galium aparine* (catchweed bedstraw)
C: *Alopecurus myosuroides* (field foxtail, black grass)
D: *Echinochloa crus-galli* (barnyard grass)
VA signifies application by the pre-germination method and NA signifies application by the post-germination method.

TABLE 3

| COMPOUND (Example No.) | Application time | Effective Amount (kg/ha) | | | |
|---|---|---|---|---|---|
| | | A | B | C | D |
| 30 | NA | <1 | <1 | 1 | 4 |
| 32 | VA | <1 | <1 | 4 | 4 |
| 33 | NA | <1 | 4 | 4 | 4 |
| 24 | NA | <1 | 4 | 4 | 4 |
| 27 | NA | <1 | <1 | 4 | 4 |
| 43 | VA | 1 | 1 | <1 | 4 |
| 35 | VA | <1 | 1.25 | <1 | 1.25 |
| | NA | <1 | <1 | <1 | <1 |
| 49 | NA | <1 | 1.25 | <1 | <1 |
| 62 | VA | 1.25 | 1.25 | 1.25 | 1.25 |
| 40 | NA | <1 | 1.25 | 1.25 | 1.25 |
| 59 | NA | 1.25 | 1.25 | 1.25 | 1.25 |
| 85 | VA | 1 | 4 | 1 | 4 |

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

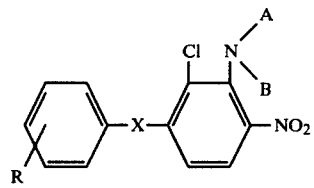

wherein
A is hydrogen, alkyl of 1 to 6 carbon atoms, cycloalkyl of 3 to 6 carbon atoms, chloro-(alkyl of 2 to 6 carbon atoms), hydroxy-(alkyl of 2 to 6 carbon atoms) or allyl;
B is alkyl of 1 to 3 carbon atoms;
R is hydrogen, fluorine, chlorine, bromine, methyl or methoxy; and
X is oxygen or sulfur.

2. The compound of claim 1 which is 2-chloro-3-phenoxy-6-nitroaniline.

3. A selective herbicidal composition consisting essentially of an inert carrier and an herbicidally effective amount of a compound of claim 1.

4. A selective herbicidal composition of claim 3 which additionally contains an herbicidally effective amount of another herbicide.

5. The method of killing weeds which comprises contacting said weeds with an effective amount of a selective herbicidal composition of claims 3 or 4.

6. The method of controlling undesirable plant growth which comprises administering an effective amount of a compound of claim 1.

* * * * *